United States Patent [19]

Vértesy et al.

[11] Patent Number: 4,990,500
[45] Date of Patent: Feb. 5, 1991

[54] OXIRANE PSEUDOOLIGOSACCHARIDES, A PROCESS FOR THEIR PREPARATION, THEIR USE AND PHARMACEUTICAL PREPARATIONS

[75] Inventors: László Vértesy, Eppstein/Taunus; Joachim Betz, Frankfurt am Main; Hans-Wolfram Fehlhaber, Idstein; Karl Geisen, Frankfurt am Main, all of Fed. Rep. of Germany

[73] Assignee: Hoechst Aktiengesellschaft, Frankfurt am Main, Fed. Rep. of Germany

[21] Appl. No.: 83,807

[22] Filed: Aug. 11, 1987

[30] Foreign Application Priority Data

Aug. 13, 1986 [DE] Fed. Rep. of Germany ....... 3627421

[51] Int. Cl.$^5$ .................... A61K 31/70; A61K 7/40; C12P 19/26
[52] U.S. Cl. ....................... 514/54; 514/23; 514/835; 514/866; 536/18.7; 536/55; 536/55.1; 536/55.3; 536/123; 435/84; 435/886; 424/50
[58] Field of Search ............. 514/54, 835, 866, 23; 536/18.7, 123, 55, 55.1, 55.3; 435/84, 886; 424/50

[56] References Cited

U.S. PATENT DOCUMENTS

| 3,876,766 | 4/1975 | Frommer et al. | 514/54 |
| 4,013,510 | 3/1977 | Frommer et al. | 435/896 |
| 4,595,678 | 6/1986 | Horii et al. | 514/53 |
| 4,618,602 | 10/1986 | Vertesy et al. | 536/123 |
| 4,632,917 | 12/1986 | Vertesy et al. | 514/54 |

FOREIGN PATENT DOCUMENTS

| 2719912 | 11/1978 | Fed. Rep. of Germany | 435/74 |
| 58-172400 | 10/1983 | Japan . | |
| 0648326 | 3/1985 | Switzerland | 536/18.7 |

OTHER PUBLICATIONS

Ohyama et al.; Agric. Biol. Chem. 41(11): 2221–2228 (1977).
Streitwieser, Jr. et al.; *Introduction to Organic Chemistry*, second edition, Macmillan Publishing Co., Inc. (1981), pp. 265–268, 1062–1065.
Yokose et al.; J. Antibiotics 36(9): 1157–1175 (1983).
Tajiri et al.; Agric. Biol. Chem. 47(4): 671–679 (1983).
Tokyotanabe; Chemical Abstracts; 100:155200x (1984), p. 421.

Primary Examiner—Ronald W. Griffin
Assistant Examiner—Nancy S. Carson
Attorney, Agent, or Firm—Finnegan, Henderson, Farabow, Garrett, and Dunner

[57] ABSTRACT

Oxirane-pseudooligosaccharides of the formula I

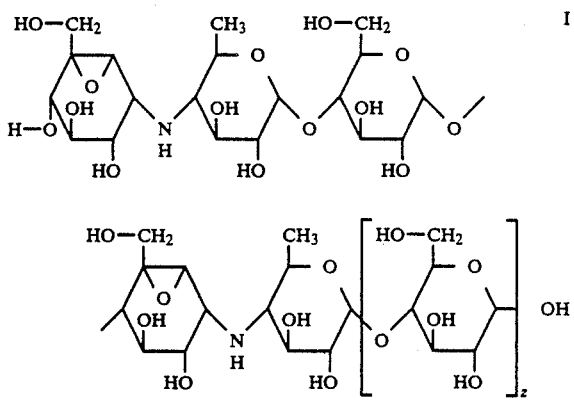

in which z is zero or 1, their physiologically acceptable salts with acids, a process for their preparation, pharmaceutical preparations, and their use are described. The compounds have an α-glucosidase-inhibiting action.

11 Claims, No Drawings

OXIRANE PSEUDOOLIGOSACCHARIDES, A PROCESS FOR THEIR PREPARATION, THEIR USE AND PHARMACEUTICAL PREPARATIONS

The invention relates to biologically active oxirane pseudooligosaccharides and their physiologically acceptable salts. They have α-glucosidase-, i.e., for example, α-amylase- and disaccharidase-inhibiting properties and can therefore be used in human and veterinary medicine, in animal nutrition and in starch biotechnology.

The European patent application having the publication No. 0,173,948 (EP-A2-0,173,948, corresponding to U.S. Pat. No. 4,632,917 the disclosures of which are incorporated herein by reference) claims pseudooligosaccharides having an α-glucosidase-inhibiting action and the formula III

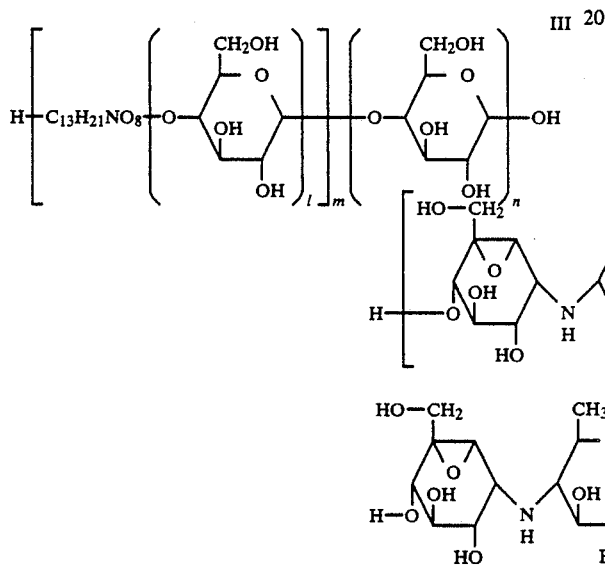

in which
l denotes 1 or 2,
m denotes 1, 2 or 3, and
n denotes an integer from 1 to 20.

The compounds described are potent inhibitors, also called W-46 type inhibitors below, which, due to their action on glucoside hydrolases of the digestive tract, can be employed as glucose-resorption retardants in the treatment of diabetes, adiposis, inter alia. They are obtained from the culture fluids of organisms which form inhibitor W-46, such as, for example, *Streptomyces galbus* subsp. FH 1716 (DSM 3007). Unary substances are obtained only by a complicated process, a mixture of various inhibitors which differ in the length of the glucose-containing chains being obtained in many cases. This non-uniformity is a handicap for reliable dosing and standardization, and is of disadvantage in the application of the preparation.

It has now been found that novel, highly-active degradation products which can easily be separated from one another using suitable methods and which can be prepared in pure form can be obtained from the original inhibitor mixture corresponding to U.S. Pat. No. 4,632,917 by acid hydrolysis or enzymatic elimination of glucose.

The invention therefore relates to oxirane-pseudooligosaccharides of the formula I

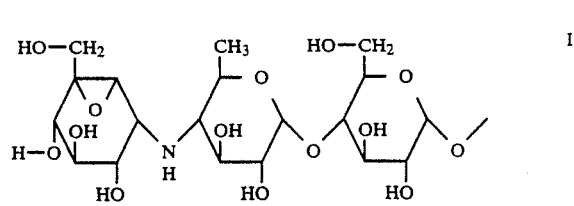

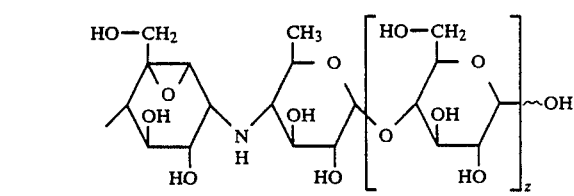

in which z is zero or 1, and their physiologically acceptable salts with acids. The two inhibitors falling under the formula I have the following formulae Ia and Ib

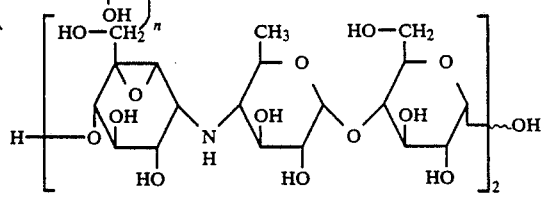

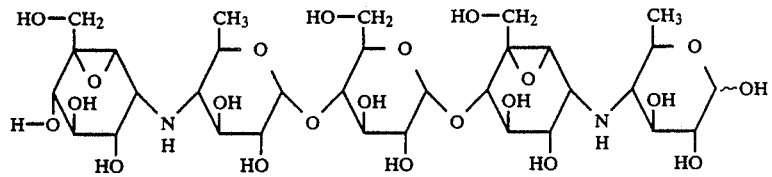

In the text below, the pseudooligosaccharide of the formula Ia and its salts are also named inhibitor W-46 H, and the pseudooligosaccharide of the formula Ib and its salts are also named inhibitor W-46 P.

The invention furthermore relates to a process for the preparation of inhibitors W-46 H and P, pharmaceutical preparations which contain these compounds and their use as medicaments, diagnostic agents and reagents.

The process for the preparation of inhibitors W-46 H and W-46 P comprises
(a) eliminating sugar from an α-glucosidase inhibitor of the formula II

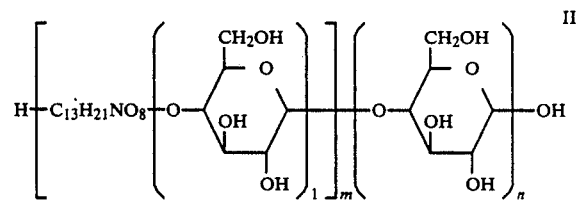

in which
m denotes 2 or 3, and
n denotes an integer from 1 to 20, or from a mixture of these inhibitors using chemical or biochemical methods, forming a compound of the formula I, or (b) cultivating, in a fermentation medium using a suitable submersion method, a Streptomycete which produces pseudooligosaccharides of the formula I, isolating and purifying the inhibitors from the mycelium or culture filtrate in a fashion which is known per se, and converting, if appropriate, the compounds of the formula I obtained into a physiologically acceptable salt.

Of the Streptomycetes, *Streptomyces galbus* subsp. FH 1716 is especially suitable for carrying out the process. This strain is filed in the Deutschen Sammlung von Mikroorganismen [German Register of Microorganisms] (DSM) under the Registration No. DSM 3007 and is described in U.S. Pat. No. 4,632,917. However, the variants and mutants of this strain can also be employed to obtain inhibitors W-46 H and W-46 P.

Inhibitors of the formula II and processes for obtaining them are described in U.S. Pat. No. 4,632,917. Unary inhibitors which are shortened in the saccharide chain are produced by the process according to the invention by eliminating sugars such as, for example, glucose.

Inhibitors W-46 H and W-46 P are preferably obtained by method a.

They are expediently obtained as follows:

The starting materials used are inhibitors of the formula II (cf. U.S. Pat. No. 4,632,917), either in enriched or in chemically purified form. However, the crude, unpurified fermentation solutions of organisms forming W-46 can also be used. The elimination of various-length glucose chains of the inhibitors is carried out, for example, by acid hydrolysis using sulfuric acid, hydrochloric acid, trifluoroacetic acid inter alia in the temperature range 0° to 120° C., preferably 80°–105° C. Depending on the temperature, the hydrolysis duration is a few minutes to several days. The procedure is preferably carried out in the range 20–200 minutes.

Another way of eliminating neutral sugars such as, for example, maltose and glucose from the inhibitors of the mixture according to U.S. Pat. No. 4,632,917 comprises using α-glucoside-cleaving enzymes. It has been found that, in contrast to enzymes in warm-blooded organisms, some microbial α-amylases are very capable of shortening, and thus making uniform, the inhibitors of the W-46 type, such as, for example, W-46 A, W-46 B or W-46 C, inter alia (cf. U.S. Pat. No. 4,632,917) by eliminating neutral sugars. Such enzymes are, for example, the α-amylase from *Bacillus subtilis* or *Bacillus licheniformis* (both particularly suitable for obtaining W-46 H), but amylases from other suitable microorganisms can also be used. α-Amylases from thermophilic or thermotolerable microorganisms whose enzymes also have a relatively high temperature optimum are preferably employed. At elevated temperatures, such amylases lead to relatively high reaction rates, i.e. to advantageous, relatively short reaction times. With the aid of such suitable enzymes, 0.01 to 20, preferably 0.5–5, percent strength inhibitor solutions can be converted in good yield. In this reaction, the pH and temperature are selected depending on the enzyme properties. The reaction can be carried out between 0° and 100° C., the range between 30° and 80° C. being preferred.

By controlling the fermentation time in the microbial preparation (according to process b) or varying the glucose elimination or hydrolysis time (according to process a), either inhibitor W-46 H or W-46 P can be obtained preferentially. The inhibitors can be isolated from the fermentation or reaction solutions and purified by processes which are known per se.

A large number of processes, such as, for example, chromatography on ion exchangers, molecular sieves or adsorption resins, in addition solvent precipitation, ultrafiltration, Craig distribution inter alia, are suitable for this purpose.

A preferred process for isolating and purifying the inhibitors W-46 H or P comprises adsorbing the inhibitors from the treated—for example as described above—culture filtrate or the reaction solution on a suitable resin, for example based on polystyrene, separating off this charged resin and isolating the inhibitors mentioned by elution with suitable buffer solutions, such as, for example, phosphate or Na acetate buffer solution, or with optionally water-containing organic solvents, such as, for example, methanol, ethanol or acetone, but preferably with aqueous isopropanol. The inhibitor-containing eluates are concentrated by ultrafiltration in a fashion which is known per se, desalination being carried out simultaneously. The low-ion aqueous solution of the inhibitors mentioned is then separated off in a fashion which is known per se by chromatography on an ion exchanger column. Strongly or weakly acidic cation exchangers, for example based on styrene-divinylbenzene copolymers, which carry as functional groups SO$_3$H or —COOH ($^R$Dowex 50 W, $^R$Amberlite CG 120) or based on modified sulfopropyl cellulose (SP-$^R$Sephadex) as ion exchanger are preferably used, but a large number of other commercially available cation exchangers can also be used. The final step in the isolation is the use of a molecular sieve, for example based on polyacrylamide gel ($^R$Biogel P-6) or based on modified cellulose ($^R$Sephadex). The resulting aqueous solutions of the pure material are then dried, for example by lyophilization.

The pure inhibitors W-46 H and W-46 P are colorless, amorphous pseudooligosaccharides. They contain nitrogen and have a weakly basic character. Thus, the inhibitors W-46 H and P migrate as cations in the direction of the cathode in high-voltage electrophoresis in acidic buffers, such as, for example, aqueous formic acid/acetic acid mixtures. The substances according to the invention have reducing properties which can be demonstrated as is conventional in sugar chemistry, for example using triphenyltetrazolium chloride (TCC).

The molecular weights, determined by FAB mass spectrometry, of the pure compounds are: 981 m/e (M+H$^+$) corresponding to the empirical formula $C_{38}H_{64}N_2O_{27}$ of the inhibitor W-46 H (free base), or 819 m/e (M+H$^+$) corresponding to the empirical formula $C_{32}H_{54}N_2O_{22}$ of the inhibitor W-46 P (free base). The formula Ia was allocated to compound W-46 H and the formula Ib to compound W-46 P on the basis of spectroscopic investigations, in particular nuclear magnetic resonance spectroscopic investigations.

Several α-glucosidase inhibitors have already been described in the literature, but only the series of compounds NS 1 to NS 17 described by H. Takeda et al. (Japanese Preliminary Published Specification 83-172,400 (Oct. 11, 1983)) contains epoxide rings (oxiranes) in the structural formulae. The epoxide structures occur only once in each case.

The compounds according to the invention differ from the inhibitors of the series NS 1 to NS 17 in the formulae Ia and Ib, in which the active epoxidepseudoamino sugar structures are present twice. Compared to the pseudooligosaccharides have an α-glucosidase-inhibiting action according to U.S. Pat. No. 4,632,917, W-46 H and W-46 P can be differentiated through the shortened saccharide chains (lower molecular weight). These are thus novel substances which have a unary structure.

Both inhibitors W-46 H and W-46 P strongly inhibit the α-amylase from the pancreas and the disaccharidases from the small intestine mucosa, in particular the saccharase which cleaves cane sugar. The specific activities are $4 \times 10^4$ α-amylase inhibitor units (AIU) per mg and $1 \times 10^4$ saccharase inhibitor unit (SIU) per mg respectively for W-46 H, and $1 \times 10^4$ AIU per mg and $3 \times 10^4$ SIU per mg respectively for the inhibitor W-46 P. The activities were determined in the following tests:

AMYLASE TEST

An amylase inhibitor unit (AIU) is defined as the amount of inhibitor which is capable of inhibiting two amylase units (AU) to 50% under the test conditions. According to international agreement, one amylase unit is the amount enzyme which cleaves 1 µequivalent of glucoside bonds in the starch in one minute. The µgram-equivalents of cleaved glucoside bonds are determined photometrically using dinitrosalicylic acid as the µgram-equivalents of reducing sugars. The data are calculated as µmoles of maltose, determined with reference to a maltose calibration line.

The tests are carried out as follows:

α-Amylase from the pig pancreas and the solutions to be tested are preincubated together at 37° C. for 10–20 minutes in 1.0 ml of 20 mM phosphate buffer, pH 6.9 + 10 mM of NaCl. The enzymatic reaction is initiated according to Zulkowski by adding 1.0 ml of soluble starch (0.25% in the buffer specified). After exactly 10 minutes, the reaction is terminated using 2.0 ml of dinitrosalicylic acid coloring reagent (according to Boehringer Mannheim: BiochemicaInformation II) and the mixture is heated for 5 minutes in a boiling water bath to develop the color. After cooling, the extinction is measured at 546 nm against the blank reagent. 50% inhibition is determined graphically compared to the uninhibited enzyme reaction by means of the probability plot by using various amounts of inhibitor.

SACCHARASE TEST

One saccharase inhibitor unit (SIU) is defined as the amount of inhibitor which is capable of inhibiting to 50% two saccharase units (SU) under the test conditions. According to international agreement, one SU is the amount of enzyme which cleaves 1 µequivalent of glycoside bonds in saccharose in one minute. The µgram-equivalents of cleaved glucoside bonds are determined photometrically using the hexokinase/glucose-6-phosphate dehydrogenase method as 2 µgram equivalents. The data are calculated as µmoles of hexoses, determined with reference to a glucose calibration curve.

The tests were carried out according to H. U. Bergmeyer, described in "Methods of Enzymatic Analysis", 3rd edition, Verlag Chemie, Weinheim, 1984, pages 96–103.

The properties of the inhibitors according to the invention are interesting with respect to use as therapeutic agents against diabetes, prediabetes and adiposis, and as a dietary support. Due to their properties, they are also valuable as reagents for diagnostic purposes.

The invention therefore also relates to medicaments, in particular those for the treatment of the disorders mentioned, and the use as medicaments, in particular as antidiabetics, and as reagents.

In animals and humans, starch- and sucrose-containing foods and nonessential items lead to an increase in blood sugar and thereby also to increased insulin secretion of the pancreas. Hyperglycemia occurs through the degradation of starch and sucrose to form glucose in the digestive tract under the action of amylase and saccharase.

In diabetics, hyperglycemia is particularly pronounced and longlasting.

Alimentary hyperglycemia and hyperinsulinemia after intake of starch and sucrose can be reduced by the inhibitors W-46 H and W-46 P according to the invention. This action depends on the dose. The α-glucosidase inhibitors according to the invention can therefore be employed as therapeutic agents in the case of diabetes, prediabetes and adiposis and for dietary support. Administration, in particular at meal times, is recommended for this purpose. The dosage, which depends on the weight of the patient and on the individual requirements, is 5–500 mg per dose, which is expediently taken at each meal time. However, the dosage can also be above or below this in substantiated individual cases.

The α-glucosidase inhibitors according to the invention are suitable, in particular, for oral administration. They can be administered as the substance per se, as its physiologically acceptable salts with acids, but also in the form of a pharmaceutical preparation using conventional auxiliaries and excipients. Combined administration with other medicaments, such as substances which reduce the blood sugar or lipid levels, may also be of advantage. Since higher-molecular-weight saccharides as such are not resorbed from the digestive tract, or not to a notable extent, no toxicologically questionable side effects are expected of the substances according to the invention.

Accordingly, it was not possible to detect striking symptoms after oral administration, even of high doses, of inhibitors W-46 H and P to experimental animals.

In order to test the pharmacological action of the α-glucosidase inhibitors, unfed, male Wistar rats weighing between 200 and 250 g were given orally an inhibitor W-46 H or W-46 P according to the invention together with 2 g of starch or sucrose per kg of body weight as a suspension in ®Tylose (methylhydroxyethylcellulose). The activity of the preparations was demonstrated by determining the blood sugar concentrations in blood samples taken before, during and after p.o. administration of the α-glucosidase inhibitors.

In these investigations, the values collated in Tables 1 (action on the blood glucose concentration of starch-fed rats) and 2 (action on the blood glucose concentration of sucrose-fed rats) were determined for inhibitor W-46 H.

TABLE 1

| Time in hours after treatment | Blood glucose in mmol/l ($\bar{x}$ ± SEM, n = 7) | | |
|---|---|---|---|
| | p.o. Dose 0.3 mg/kg | p.o. Dose 1.0 mg/kg | Control |
| 0 | 3.77 ± 0.09 | 3.93 ± 0.10 | 3.79 ± 0.14 |
| 0.5 | 5.53 ± 0.17 | 5.04 ± 0.08 | 5.56 ± 0.16 |
| 1 | 5.59 ± 0.06 | 5.07 ± 0.09 | 6.36 ± 0.17 |
| 2 | 5.67 ± 0.13 | 4.99 ± 0.14 | 5.18 ± 0.17 |
| 3 | 4.86 ± 0.18 | 4.57 ± 0.10 | 4.94 ± 0.16 |

TABLE 1-continued

| Time in hours after treatment | Blood glucose in mmol/l ($\bar{x} \pm$ SEM, n = 7) | | |
|---|---|---|---|
| | p.o. Dose 0.3 mg/kg | p.o. Dose 1.0 mg/kg | Control |
| 5 | 4.39 ± 0.13 | 4.13 ± 0.08 | 4.19 ± 0.14 |

TABLE 2

| Time in minutes after treatment | Blood glucose in mmol/l ($\bar{x} \pm$ SEM, n = 7) | | | |
|---|---|---|---|---|
| | p.o. Dose 1 mg/kg | p.o. Dose 3 mg/kg | p.o. Dose 10 mg/kg | Control |
| 0 | 3.99 ± 0.10 | 3.94 ± 0.14 | 4.01 ± 0.15 | 4.08 ± 0.12 |
| 15 | 6.07 ± 0.28 | 5.71 ± 0.23 | 5.06 ± 0.20 | 6.65 ± 0.40 |
| 30 | 6.01 ± 0.22 | 5.53 ± 0.19 | 5.11 ± 0.10 | 6.63 ± 0.10 |
| 60 | 6.34 ± 0.14 | 5.47 ± 0.15 | 4.82 ± 0.09 | 7.18 ± 0.30 |
| 120 | 5.45 ± 0.13 | 5.20 ± 0.16 | 4.50 ± 0.11 | 5.50 ± 0.09 |
| 240 | 4.57 ± 0.07 | 4.83 ± 0.15 | 4.29 ± 0.22 | 4.90 ± 0.07 |

A limiting value of 0.27 mg/kg of rat is calculated from the values given in Table 1 and a limiting value of 1.29 mg/kg of rat from the values given in Table 2 (the limiting value of the active ingredient is taken to mean the amount per kg of experimental animal at whose administration a clear action can still be seen after one hour).

Besides blood glucose regulation, the oligosaccharides according to the invention can also be used to inhibit saliva α-amylase. This enzyme causes digestion of starch in the mouth, and the sugars thus formed promote caries attack on the teeth. The compounds according to the invention can therefore be used for preventing or reducing the formation of caries.

Furthermore, they can be used as biochemical reagents and as diagnostic agents.

EXAMPLE 1

5.0 g of inhibitor mixture containing components W-46 A, W-46 B and W-46 C, obtained according to the data in U.S. Pat. No. 4,632,917 (Examples 1 and 2), are dissolved in 80 ml of 2N trifluoroacetic acid and heated at 100° C. for 10 minutes with exclusion of oxygen. After this time has passed, the reaction vessel is cooled rapidly with stirring, and the aqueous trifluoroacetic acid is removed to dryness by distillation in vacuo.

In order to obtain the shortened inhibitors, the solid distillation residue is dissolved in distilled water and transferred onto a 3 liter column packed with ion exchanger SP-Sephadex$^R$ C-25 and equilibrated to pH 3. The active ingredient is eluted by applying an increasing 50 mM NaCl gradient. Whereas an NaCl concentration having a conductivity of 3.0 mS removes the inhibitor W-46 H from the column, elution of the compound W-46 P occurs at a conductivity of 4 mS. For desalination, the separately collected eluates are concentrated by ultrafiltration at ≧35 bar and subsequently freeze-dried. 0.7 g of inhibitor W-46 H and 1.6 g of inhibitor W-46 P (in each case as the hydrochloride) are produced.

EXAMPLE 2

65 g of inhibitor mixture, obtained according to U.S. Pat. No. 4,632,917 (Examples 1 and 2), are dissolved in 6.5 liters of water, and the pH is adjusted to 7.5. 1 g of α-amylase from Bacillus subtilis 130 U/mg is subsequently added, and the mixture is stirred at 60° C. for 18 hours. During this time, it is ensured that the pH remains constant. When the reaction time is complete, the resultant solution is filtered at room temperature through 4 liters of 20 polystyrene adsorption resin (®Diaion HP-20). Whereas the so-called eluate contains the undesired contaminants, neutral sugars and salts, inhibitor W-46 H is obtained by washing the column with 20 liters of 10% strength isopropanol solution. Drying leads to the desired inhibitor. If the compound W-46 H is not produced purely enough at this point, further purification can be carried out on ion exchangers, as described in Example 1.

EXAMPLE 3

10 g of inhibitor W-46 H, obtained according to Example 1, are dissolved in 200 ml of water and filtered through 200 ml of anion exchanger IRA-68, OH form, which is packed in a glass column. The column is subsequently washed with 200 ml of water. The eluates are combined. They contain the inhibitor in the form of the free base. The solution is now divided into four equal parts. A quarter is in each case adjusted to pH 6 using glucuronic acid or sulfuric acid or hydrochloric acid and freeze-dried, as is the fourth quarter, which is not neutralized. After drying, the latter solution gives 2.3 g of W-46 H (free base) with $4 \times 10^4$ AIU/mg and $1 \times 10^4$ SIU/mg, and the other solutions give 2.5 g of W-46 H containing glucuronic acid (=W-46 H glucuronate), specific activity $3.6 \times 10^4$ AIU/mg and $9 \times 10^3$ SIU/mg, 2.4 g of W-46 H containing sulfuric acid (=W-46 H sulfate), specific activity $3.8 \times 10^4$ AIU and $9.6 \times 10^3$ SIU/mg, and 2.34 g of W-46 H containing hydrochloric acid (=W-46 H chloride), specific activity $3.9 \times 10^4$ AIU/mg and $1 \times 10^4$ SIU/mg respectively.

EXAMPLE 4

10 g of α-glucosidase inhibitor W-46 P according to Example 1 are treated as described in Example 3 with W-46 H. 2.4 g of W-46 P free base with $1 \times 10^4$ AIU/mg and $3 \times 10^4$ SIU/mg are produced.
2.6 g of W-46 P glucuronate,
2.3 g of W-46 P sulfate;
2.3 g of W-46 P chloride.

We claim:
1. An oxirane-pseudooligosaccharide of the formula I

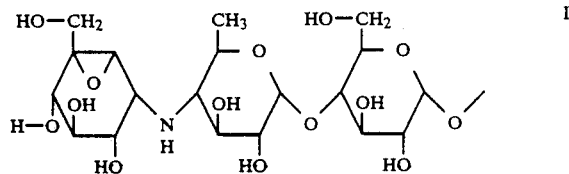

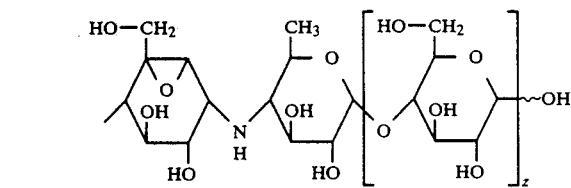

in which z is zero or 1, and its physiologically acceptable salts with acids.

2. A process which comprises (a) eliminating sugar from an α-glucosidase inhibitor of the formula II

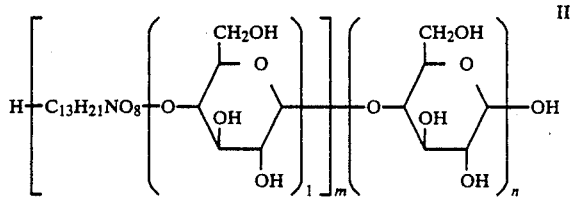

in which m denotes 2 or 3, and n denotes an integer from 1 to 20, or from a mixture of these inhibitors, using acid hydrolysis or enzymatic cleavage to form a compound of the formula I as set forth in claim 1 or a physiologically acceptable salt thereof.

3. A pharmaceutical preparation for inhibiting α-glucosidase which comprises an oxirane-pseudooligosaccharide as claimed in claim 1 or a physiologically acceptable salt thereof together with a pharmaceutically acceptable carrier.

4. A method of inhibiting α-glucosidase in a host, which comprises administering to said host an effective amount of an oxirane-pseudooligosaccharide as claimed in claim 1 or a physiologically acceptable salt thereof for said inhibition, with or without a pharmaceutically acceptable carrier.

5. A method for treating diabetes, prediabetes or adiposis in a host which comprises administering to said host an effective amount of an oxirane-pseudooligosaccharide as claimed in claim 1 for said treatment, with or without a pharmaceutically acceptable carrier.

6. A method of using an oxirane-pseudooligosaccharide as claimed in claim 1 or a physiologically acceptable salt thereof as a prophylactic against caries which comprises administering an effective amount of said compound to a host, with or without a pharmaceutically acceptable carrier.

7. A process for the preparation of an oxirane-pseudooligosaccharide as claimed in claim 1 or a physiologically acceptable salt thereof, which comprises cultivating in a fermentation medium a Streptomycete which produces said pseudooligosaccharide and isolating and purifying said pseudooligosaccharide from said medium.

8. The process of claim 2, wherein said elimination of sugar comprises acid hydrolysis.

9. The process of claim 2, wherein said elimination of sugar comprises enzymatic cleavage.

10. The process of claim 9, wherein the enzyme is a microbial α-amylase.

11. The process of claim 7, wherein the fermentation medium is mycelium or a cultured filtrate.

* * * * *